United States Patent [19]

Evans et al.

[11] Patent Number: 5,494,155
[45] Date of Patent: Feb. 27, 1996

[54] INCORPORATION OF ABSORBENTS DURING EXTRACTION AND/OR HYDRATION OF HYDROGEL MATERIALS USED AS OPHTHALMIC DEVICES

[75] Inventors: John M. Evans, Fremont; William E. Meyers, San Ramon; Joseph Weinschenk, Laguna Niguel, all of Calif.

[73] Assignee: Pilkington Barnes Hind, Inc., Sunnyvale, Calif.

[21] Appl. No.: 269,163

[22] Filed: Jun. 29, 1994

[51] Int. Cl.$^6$ .............. B65D 81/26; B29D 11/00
[52] U.S. Cl. ............ 206/204; 206/210; 206/51; 264/26
[58] Field of Search ............... 264/2.6; 206/204, 206/210, 5.1

[56]    References Cited

U.S. PATENT DOCUMENTS

| | | | |
|---|---|---|---|
| 4,955,580 | 9/1990 | Seden et al. | 249/82 |
| 5,036,971 | 8/1991 | Seden et al. | 264/2.6 |
| 5,080,839 | 1/1992 | Kindt-Larsen | 264/2.6 |
| 5,292,372 | 3/1994 | Swaisgood et al. | 134/1 |
| 5,310,568 | 5/1994 | Lini et al. | 426/422 |
| 5,312,586 | 5/1994 | Stockel | 422/37 |

*Primary Examiner*—Mark D. Sweet
*Attorney, Agent, or Firm*—Burns, Doane, Swecker & Mathis

[57]    ABSTRACT

Disclosed are methods for extracting leachable materials from a hydratable polymer by incorporation of an adsorbent into the solution employed to effect extraction. Suitable adsorbents are characterized as having a higher affinity for the leachable materials than either the hydratable polymer or the solvent employed in the solution. Also disclosed are sealed packages comprising an aqueous solution, an adsorbent and a hydratable polymer in the form of an ophthalmic device.

23 Claims, 1 Drawing Sheet

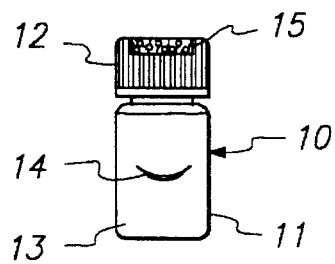
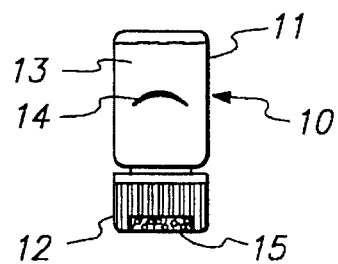
FIG. 1A                FIG. 1B
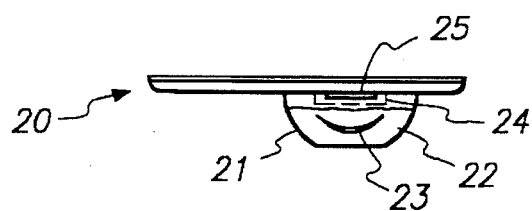
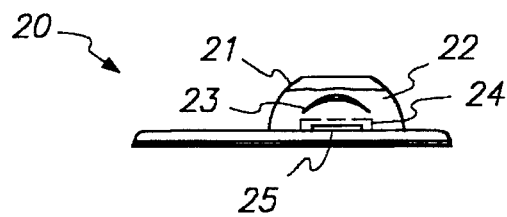
FIG. 2A                FIG. 2B
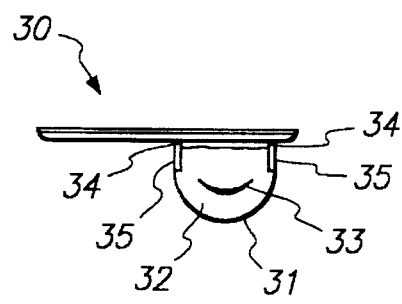
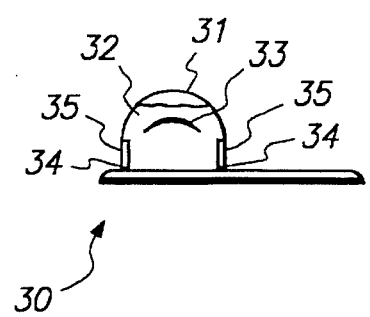
FIG. 3A                FIG. 3B

INCORPORATION OF ABSORBENTS DURING EXTRACTION AND/OR HYDRATION OF HYDROGEL MATERIALS USED AS OPHTHALMIC DEVICES

BACKGROUND OF THE INVENTION

1. Field of the Invention

This invention is directed to methods for extracting leachable materials from a hydratable polymer such as a xerogel material. In one embodiment, the extraction is conducted after hydration of the hydratable polymer. In another embodiment, extraction is conducted simultaneously with hydration of this polymer to a hydrogel material. In either case, the resulting hydrogel material can then be used in ophthalmic devices such as intraocular lenses, contact lenses, etc.

In the methods of this invention, extraction procedures are simplified by incorporation of an adsorbent into the solution which facilitates extraction of the leachable materials from the hydratable polymer. When the extraction solution is water and the hydratable polymer is in its xerogel form, hydration of the hydratable polymer to the hydrogel material occurs simultaneously with extraction.

This invention is further directed to a sealed package for shipping/storing hydrogel materials in the form of ophthalmic devices which incorporates water and an adsorbent into the package which adsorbent effects selective retention of leachable components from the ophthalmic device. These packages are particularly useful for in situ conversion of a xerogel material to a hydrogel material in the form of an ophthalmic device with concomitant extraction of the leachable components from the device. When so employed, the xerogel form of the ophthalmic device can be directly packaged and shipped for consumer use while permitting hydration and extraction to occur in situ thereby providing for a hydrated ophthalmic device suitable for consumer use.

2. State of the Art

The preparation of hydrogel ophthalmic devices, e.g., soft contact lenses, for consumer use is a multi-step process. In addition to the important concerns relating to manufacturing a contact lens or other ophthalmic device which is appropriately fitted for the particular consumer's needs, the ophthalmic device manufacturing process must include process steps for removal of leachable materials from the hydratable polymer used in the device.

Specifically, soft hydrogel ophthalmic devices are prepared by polymerizing a monomeric composition to a dry hydratable polymer typically referred to in the an as a "xerogel" or a "xerogel material". The as-prepared xerogel material typically contains leachable materials such as unreacted monomers and partially reacted oligomers. Contamination of the xerogel material with such monomers and oligomers is undesirable since these materials are toxic and, during use, can leach into the eye fluid causing, for example, eye irritation and other problems. Accordingly, the U.S. Food and Drug Administration (FDA) has set standards relative to maximum monomer/oligomer concentration in ophthalmic devices for consumer use. In order to meet these standards, a portion of the leachable materials must be removed from the polymer composition which removal is typically achieved by several washings of the ophthalmic devices using water, ethanol, or other suitable solvents. When using such solvents, a portion of the leachable materials, including the unreacted monomers and partially reacted oligomers, are transferred under a mass-transfer mechanism to the solvent which solvent is subsequently discarded. This washing step is repeated until leachable contamination in the ophthalmic device is reduced to acceptable levels.

When water is used as the washing material, the washing steps also result in hydration of the hydratable polymer from its xerogel to its hydrogel form. When ethanol or other non-aqueous solvents are employed in the washing steps, then a separate hydration step is afterwards required to form the final hydrogel.

After extraction/hydration, the ophthalmic device is typically inserted into a sealed package containing an aqueous buffered solution for shipment and storage prior to consumer use. The inclusion of the aqueous buffered solution in the package is necessary to insure against dehydration of the hydrated ophthalmic device.

In any event, the process of effecting formation of a hydrated ophthalmic device from a hydratable polymer in the form of a xerogel material involves numerous extraction/hydration steps which necessarily hinder efficient manufacture of ophthalmic devices prior to packaging of these devices into end use form. Additionally, the presence of leachable materials in the discarded solvent can cause disposal problems.

In addressing this problem, the art has described methods which result in the extraction of leachable materials to a desired level. For example, Kindt-Larsen, U.S. Pat. No. 5,080,839, discloses a process wherein the contact lens is placed into a cavity defined by a first and a second carrier element which both confines and maintains a proper orientation for the lens. A fluid flow is then introduced through the cavity to effect flushing of the leachables from the lens which fluid flow can be repeated as necessary to effect reduction of the leachables to a desired level. Allegedly, the use of such a fluid flow through this cavity results in more efficient removal of the leachables from the lens and reduces the need to physical manipulate the lens while maintaining a proper orientation of the lens in the cavity.

However, notwithstanding the advantages of this method, there is a continuing need in the art to simplify the extraction/hydration steps required to form an ophthalmic device having acceptable contaminant (i.e., leachable material) concentration. In this regard, it would be particularly advantageous if the extraction/hydration step could be coupled with a packaging step so as to provide for an overall efficient method for preparing and packaging an ophthalmic device for consumer use.

SUMMARY OF THE INVENTION

This invention is based, in part, on the discovery that methods for the extraction of leachable materials from an ophthalmic device can be greatly simplified by the inclusion of an adsorbent into the extraction solution which adsorbent effects selective retention of leachable materials from the ophthalmic device.

Accordingly, in one of its method aspects, this invention is directed to a method for extracting leachable materials from a hydratable polymer in the form of an ophthalmic device which method comprises:

(a) incorporating an adsorbent into an aqueous solution; and (b) contacting the hydratable polymer with the solution produced in (a) above and maintaining said polymer in such contact under conditions sufficient to reduce the concentration of said leachable material in said polymer.

In this embodiment, the hydratable polymer can be in its xerogel form, its hydrogel form or can be in an organic solvent swollen form wherein the organic solvent is a hydrophilic solvent having a boiling point of about 40° C. and above. Such solvents are non-reactive with the hydratable polymer and, include by way of example, methanol, ethanol, ethylene glycol, glycerol, N-methyl pyrrolidone, methylene chloride, boric acid esters of polyhydric alcohols and dihydric alcohols and the like.

This invention is also based, in part, on the discovery that the hydratable polymer can be contacted with the aqueous solution prior to incorporation of the adsorbent. Accordingly, in another of its method aspects, this invention is directed to a method for extracting leachable materials from a hydratable polymer in the form of an ophthalmic device which method comprises:

(a) incorporating an adsorbent into an aqueous solution comprising water and a hydratable polymer; and (b) maintaining said polymer in said aqueous solution under conditions sufficient to reduce the concentration of said leachable material in said polymer.

This invention is still further based, in part, on the discovery that when the hydratable polymer is in its xerogel form, inclusion of such an adsorbent into the solution simultaneously effects extraction of leachable materials from the hydratable polymer as well as hydrates the polymer composition to its hydrogel form.

Accordingly, in another of its method aspects, this invention is directed to a method for extracting leachable materials from a hydratable polymer in the form of an ophthalmic device and hydrating said polymer which method comprises:

(a) incorporating an adsorbent into an aqueous solution; and (b) immersing a hydratable polymer in its xerogel form into the solution produced in (a) above and maintaining said polymer in said solution under conditions sufficient to reduce the concentration of said leachable materials from said polymer and to hydrate said polymer.

The method for simultaneously extracting leachable materials from the hydratable polymer and hydrating the polymer to a hydrogel material in the form of an ophthalmic device is particularly useful for in situ conversion of the hydratable polymer from its xerogel form to its hydrogel form in a sealed package thereby facilitating overall manufacturing and shipment procedures. In this embodiment, this invention is directed to a sealed package comprising an aqueous solution, a hydratable polymer in the firm of an ophthalmic device and an adsorbent wherein said package contains sufficient solution to immerse said polymer and further wherein said adsorbent has a higher affinity for the leachable materials than either the hydratable polymer or the solution.

In a preferred embodiment, the adsorbent is separated from the hydratable polymer. Such separation can comprise physical separation where, for example, the adsorbent is physically isolated from the hydratable polymer by a permeable barrier or chemical separation where, for example, the adsorbent can comprise a second solvent non-miscible with the first solvent (e.g., the use of methylene chloride as the adsorbent in an aqueous environment).

BRIEF DESCRIPTION OF THE DRAWINGS

FIG. 1A and FIG. 1B illustrate a sealed vial containing water, an adsorbent and a hydratable polymer in the form of an ophthalmic device for the in situ extraction of leachables from the polymer and hydrating the polymer to a hydrogel material wherein the packaging is suitable for shipment and storage of the ophthalmic device to the consumer.

FIG. 2A and FIG. 2B illustrate one embodiment of a sealed blister package in different positions which package contains water, an adsorbent and a hydratable polymer in the form of an ophthalmic device for the in situ extraction of leachables from the polymer and hydrating the polymer to a hydrogel material wherein the packaging is suitable for shipment and storage of the ophthalmic device to the consumer.

FIG. 3A and FIG. 3B illustrate another embodiment of a sealed blister package in different positions which package contains water, an adsorbent and a hydratable polymer in the form of an ophthalmic device for the in situ extraction of leachables from the polymer and hydrating the polymer to a hydrogel material wherein the packaging is suitable for shipment and storage of the ophthalmic device to the consumer.

DETAILED DESCRIPTION OF THE INVENTION

This invention is directed to methods for extracting leachable materials from a hydratable polymer by incorporation of an adsorbent into the solution employed to effect extraction. However, prior to describing this invention in further detail, the following terms will first be defined.

Definitions

As used herein, the following terms have the meanings set forth below. If not defined, the terms have their art recognized meanings.

The term "leachable materials" refer to materials contained in a hydratable polymer which can be extracted from the polymer into a solvent such as water or an organic solvent such as ethanol. Typically, extraction of the leachable material into the solvent system is achieved by mass balance principles wherein an equilibrium concentration of the leachable material is achieved between the solvent and hydratable polymer phases. In practice, the leachable materials in the hydratable polymer are typically unreacted monomer used to prepare the hydratable polymer and/or partially reacted oligomers which have a degree of water solubility and are small enough to migrate through the polymer phase into the solvent phase. Partially reacted oligomers are preferably characterized as having no more than about 50 monomer units and more preferably as having a molecular weight of less than about 5,000.

The term "hydratable polymer" refers to polymer compositions which, after polymer formation, are hydratable when treated with water and, accordingly, can incorporate water into the polymeric matrix without itself dissolving in water. Hydratable polymers include such polymer compositions in either their non-hydrated or hydrated state. Hydratable polymer compositions include polymers prepared in the presence of a non-aqueous solvent or post-treated with a non-aqueous solvent wherein the non-aqueous solvent can be exchanged with water.

Preferably, the hydratable polymers are capable of incorporating at least about 10 weight percent water, and preferably from about 10 to about 95 weight percent water, into the polymer composition based on the total weight of the polymer composition. As known per se in the art, hydratable polymers are prepared by incorporation of one or more hydrophilic monomers into the polymer composition.

The term "dry polymer composition" refers to a hydratable polymer composition in its non-hydrated state which is typically formed by polymerization of the monomer composition in the absence of added water wherein any water in the resulting polymer composition is usually due to traces of moisture present in one or more of the reagents used to prepare the polymer composition. Such moisture is typically less than 1 weight percent of the total polymer composition and preferably less than 0.1 weight percent. Such compositions are also referred to as "xerogel polymer compositions" or "hydratable polymer in a xerogel form".

The term "adsorbent" refers to any material having a greater affinity for at least one of the leachable materials as compared to both the solution employed to remove the leachable materials and the hydratable polymer. In this regard, the term "adsorbent" is not intended to imply any physical or chemical mechanism for effecting affinity of the leachable material to the adsorbent and any adsorbent which possesses such affinity is suitable for use herein regardless of whether the affinity is achieved by adsorption, absorption, ionic interactions, covalent binding, or any other mechanism.

Suitable adsorbents for use herein include, by way of example, activated carbon, silica gel, an organic solvent forming a two phase system with water such as methylene chloride, chloroform, and the like. Combination of adsorbents can be used to effect reduction of the leachable materials to suitable levels. In a preferred embodiment, an adsorbent material or combination of adsorbent materials is employed which, when used in sufficient amounts, will reduce the amount of leachable materials in the hydratable polymer after treatment to a level of less than about 10 ppm.

The term "aqueous solution" refers to solutions based primarily on water but which can comprise up to about 5 weight percent of a miscible organic solvent. It is contemplated that the inclusion of such a miscible organic solvent in the aqueous solution can facilitate the removal of the leachable materials from the polymer composition. Insofar as the adsorbent material can adhere the organic solvent, an aqueous solution employing such a miscible organic solvent is preferably contacted with the hydratable polymer prior to addition of the adsorbent to the solution.

Suitable miscible organic solvents are those which will not chemically react with or solubilize to any significant extent the hydratable polymer in either its xerogel or hydrogel forms. Suitable solvents are well known in the art and include, by way of example, water, methanol, ethanol, ethylene glycol, glycerol, N-methyl pyrrolidone, methylene chloride, boric acid esters of polyhydric alcohols and dihydric alcohols and the like. Suitable polyhydric alcohols and dihydric alcohols are disclosed in U.S. Pat. Nos. 4,495,313 and 5,039,459 both of which are incorporated herein by reference in their entirety.

The term "hydrophilic ethylenically unsaturated monomer" refers to monomers which when incorporated in sufficient amounts into a polymer will render the polymer hydratable, i.e., will permit the polymer to absorb at least 10% water. Such monomers are well known in the art and the use of any such monomer is not critical. Suitable hydrophilic ethylenically unsaturated monomers suitable for use herein include, by way of example only, hydroxy lower alkyl acrylates or methacrylates, hydroxy lower alkoxy lower alkyl acrylates or methacrylates, and alkoxy lower alkyl acrylates or methacrylates. "Lower alkyl" or "lower alkoxy" is herein defined to mean an alkyl or alkoxy having from 1 to 6 carbon atoms. Specific hydrophilic monomers include hydroxyethyl methacrylate (HEMA), hydroxyethylacrylate, hydroxypropyl methacrylate, hydroxypropyl acrylate, butanediol monomethacrylate monoacrylate, glyceryl acrylate, glyceryl methacrylate, vinylpyrrolidone, N,N-dimethylacrylamide, and the like. The hydroxyalkyl acrylates and methacrylate, particularly 2-hydroxyethyl methacrylate are generally preferred.

The term "ethylenically unsaturated monomers free of hydrophilic functionality" refers to comonomers conventionally employed in combination with a hydrophilic ethylenically unsaturated hydrophilic monomer in the preparation of hydratable polymers suitable for use in contact lenses which monomers are free of hydrophilic functionality. Such monomers include styrene, acrylates or methacrylates such as methyl methacrylate, ethyl acrylate, isopropyl acrylate, propyl acrylate, butyl acrylate, sec-butyl acrylate, pentyl acrylate, 2-ethylhexyl acrylate, methyl methacrylate, ethyl methacrylate, propyl methacrylate, isopropyl methacrylate, butyl methacrylate, sec-butyl methacrylate, pentyl methacrylate, cyclohexyl methacrylate and fluorinated acrylates and methacrylates such as trifluoromethyl methacrylate, trifluoromethyl acrylate, 2',2', 2'-trifluoroethyl methacrylate, 2',2',2'-trifluoroethyl acrylate, 1,1,1,3,3,3-hexafluoroisopropyl methacrylate, etc., aryl acrylates and methacrylates such as phenyl acrylate, phenyl methacrylate, etc. Other suitable monomers include allyl or aryl vinyl ethers such as ethyl vinyl ether, phenyl vinyl ether, and the like.

Methods

The methods of this invention effect removal of leachable materials from hydratable polymers by incorporating an adsorbent into an aqueous solution and contacting the hydratable polymer with this solution under conditions sufficient to reduce the concentration of said leachable material in said polymer.

The aqueous solution, including any miscible organic solvent employed therein, should be compatible with the hydratable polymer to the extent that the solution will not (1) degrade (e.g., dissolve) the hydratable polymer; (2) chemically react with the hydratable polymer; and (3) alter its physical or chemical properties so that the hydratable polymer is no longer suitable for use as an ophthalmic device. The aqueous solution can be limited to contain only water, but preferably, aqueous solution can comprise additional components such as buffers, salts, etc., suitable for use in contact lens wear. A particularly preferred solution for use herein is an aqueous saline solution buffered to a pH of from about 6 to 8, more preferably from about 6.2 to 7.7 and still more preferably from about 6.5 to 7.5. The particular buffers and salts employed are not critical.

An adsorbent is then incorporated into the selected solution. Typically, the amount of adsorbent employed is sufficient for the intended purpose, i.e., to remove leachable materials from the selected solution and, hence, from the hydratable polymer. In a preferred embodiment, at least about 1 gram of adsorbent is employed per gram of hydratable polymer to be treated. The upper limit on the amount of adsorbent is governed solely by physical constraints and costs considerations. Typically, however, no more than about 5 grams of adsorbent is employed per gram of hydratable polymer. The exact amount of adsorbent employed is governed by the relative affinity of the leachable materials to the adsorbent, the amount of leachable materials to be removed, etc. Such factors can be readily determined by the skilled artisan.

A hydratable polymer, preferably in its xerogel form, is then contacted with the solution comprising the adsorbent produced as above or, alternatively, with the aqueous solution prior to addition of the adsorbent. However, hydratable polymers, including those in their hydrogel forms or in an organic solvent swollen form can also be employed in the methods described herein to effect removal of leachable materials therefrom.

Contact of the polymer with this solution is then maintained under conditions sufficient to reduce the concentration of said leachable material from said polymer. Preferably, contact of the hydratable polymer with this solution is achieved by immersing the polymer in the solution. However, other embodiments where the polymer contacts the solution can also be employed and include, by way of example, where the solution wicks the polymer; where the polymer is contacted with a bibulous material containing said solution; and the like.

The contacting conditions employed are not critical and the contact conditions are selected to be sufficient for the intended purpose, i.e., to remove leachable materials from the selected solution. Preferably, however, the hydratable polymer is contacted with this solution at a temperature of from above about 0° C. to about 150° C. for a period of from about 10 to about 60 minutes. In a particularly preferred embodiment, elevated temperatures, e.g., from about 40° C. to about 150° C., can be employed to accelerate the extraction process.

Preferably, the adsorbent employed is separated from the hydratable polymer so as to avoid contamination of the polymer with the adsorbent which can be troublesome if the adsorbent is in the form of fine particles. Such separation can be achieved by conventional means such as by incorporating the adsorbent into a solution permeable membrane, physically entrapping the adsorbent into the walls of the container, and the like.

The hydratable polymer employed is not critical provided that it can incorporate at least about 10 weight percent water upon hydration. As is well known in the art, such hydratable polymers are formed by use of a hydrophilic ethylenically unsaturated monomer during polymer formation. Such monomers are employed in a range from about 1 to 100 weight percent based on the total amount of monomer with the balance being ethylenically unsaturated monomer(s) free of hydrophilic functionality. The specific amounts of each monomer selected are dependent upon the desired properties for the resulting polymer composition including an ability of the polymer composition to incorporate at least about 10 weight percent water which, in turn, depends upon the relative hydrophilicity of the hydrophilic ethylenically unsaturated monomer as well as the relative hydrophilicity of any other comonomers and the relative amounts of each in the resulting polymer. Such factors are readily ascertainable by the skilled artisan. Due to this ability to incorporate water, the resulting polymer composition is often referred to as a "hydrogel" or "hydrogel material".

While hydrogels derived from a single monomer can be used, copolymeric, terpolymeric, etc. hydrogels are typically employed because the use of more than one monomer provides a ready vehicle to tailor a broad range of properties in the final product for its intended use. Examples of copolymeric or higher hydrogels include the polymer compositions set forth in the table below:

| Monomer A | Monomer B | Monomer C | Monomer D |
|---|---|---|---|
| MMA | DMA | EGDMA | — |
| MMA | DMA | EGDMA | — |
| HEMA | NVP | MAA | — |
| MMA | NVP | AMA | — |
| MMA | GMA | EGDMA | — |
| HEMA | DMA | MMA | TMPTMA |
| HEMA | DMA | MMA | TMPTMA |
| HEMA | EGDMA | — | — |
| HEMA | MMA | NVP | DVB |

AMA = allyl methacrylate
DMA = dimethylacrylamide
DVB = divinyl benzene
EGDMA = ethylene glycol dimethylacrylate
GMA = glyceryl methacrylate
HEMA = hydroxyethyl methacrylate
MMA = methylmethacrylate
NVP = N-vinylpyrrolidone
TMPTMA = trimethylolpropane trimethacrylate Commercially available copolymers, terpolymers, etc. suitable for use herein include tetrafilcon A, polymacon, bufilcon A, crofilcon A, surfilcon A, perfilcon A, netrafilcon A, and the like.

Also, as is apparent from the above, the hydratable polymer can optionally be cross-linked.

Figures

Certain aspects of this invention can be better understood by reference to the attached figures. Specifically, in FIG. 1A and FIG. 1B, a vial 10 comprising a glass container 11 and cap 12 which is fitted onto container 11 by conventional means, e.g., a screw cap which mates with the opening of container 11 (not shown), to form a water proof seal. Glass container 11 contains a selected solution 13 which, in this embodiment, is water, and a hydratable polymer 14 in the form of a contact lens. A water permeable membrane 15 shown in the cut away portion of cap 2 contains adsorbent therein. Extraction of leachable materials from hydratable polymer 14 and selected solution 13 by the adsorbent is achieved by inverting closed vial 10 thereby contacting the adsorbent with the selected solution 13 as illustrated in FIG. 1B. The adsorbent's greater affinity for the leachable material as compared to hydratable polymer 14 and selected solution 13 results in a portion of the leachable material becoming bound to the adsorbent. The amount of leachable material removed by the adsorbent is dependent upon the degree of leachable material contamination in the hydratable polymer, the relative affinity of the adsorbent for this material and the amount of adsorbent employed. Each of these factors is well within the skill of the art.

In one embodiment, after inverting vial 10, the vial contents are sterilized which not only kills any microorganisms contaminating the vial but also will accelerate the removal of leachable materials by the adsorbent.

In FIG. 2A and FIG. 2B, blister package 20 comprises a well 21 which contains an aqueous solution 22, a hydratable polymer 23 in the form of a contact lens, a water permeable membrane 24 and an adsorbent 25. In the embodiment depicted in FIG. 2A, hydratable polymer 23 is immersed in the aqueous solution 22 but neither polymer 23 nor aqueous solution 22 contacts the adsorbent 25. As shown in FIG. 2B, by inverting blister package 20, aqueous solution 22, and hence polymer 23, are now in communication with adsorbent 25. In a preferred embodiment, blister package 20 is packaged in the position shown in FIG. 2A and is sterilized in the position shown in FIG. 2B.

In one embodiment, blister package 20 is configured to be sufficiently transparent to permit inspection and measurement of the hydratable polymer 23 within the sealed package.

FIG. 3A and FIG. 3B illustrate a different configuration for a blister package 30 which comprises a well 31 containing an aqueous solution 32, a hydratable polymer 33 in the form of a contact lens, a water permeable membrane 34 and an adsorbent 35. In the embodiments depicted in FIG. 3A and FIG. 3B, hydratable polymer 33 is immersed in the aqueous solution 32 which contacts the adsorbent 35 in both instances. In a preferred embodiment, blister package 30 is packaged in the position shown in FIG. 3A and is sterilized in the position shown in FIG. 3B.

In another embodiment, a female mold half as described in FIG. 6b of U.S. Pat. No. 4,955,580 can be used to prepare a contact lens from a hydratable polymer in its xerogel form which mold portion can be used in packaging and shipping the contact lens. The closure element illustrated in FIG. 6a of U.S. Pat. No. 4,955,580 can be used with the female mold half so as to form a water tight seal for packaging and storage. The disclosure of U.S. Pat. No. 4,955,580 is incorporated herein by reference in its entirety.

The following examples illustrate certain embodiments of the invention and are not meant to limit the scope of the claims in any way.

In the following examples, the following abbreviations have the meanings set forth below. If not defined, the abbreviation has its art recognized meaning.

cm=centimeter
DMA=dimethyl acrylamide
GMA=glyceryl methacrylate
GPC=gel permeation chromatography
HEMA=hydroxyethyl methacrylate
HPLC=high performance liquid chromatography
kg=kilogram
mL=milliliters
MMA=methyl methacrylate
NVP=N-vinyl pyrrolidone
psi=pounds per square inch
µM=microns or micrometers

EXAMPLES

Example 1 below sets forth a simple procedure for evaluating whether a candidate material is a suitable adsorbent for the purposes of this invention. Example 2 demonstrates the correlation between level of leachable material contamination in the hydratable polymer and the area under the HPLC peaks. Examples 3 and 4 illustrate methods for using adsorbents for the purpose of removing impurities from polymer compositions. Examples 5 and 6 illustrate that the methods described herein can be employed in combination with packaging of a contact lens made from a hydratable monomer so as to effect both hydration of the lens and removal of the leachable materials. Example 7 illustrates the advantage of heating during the adsorption process so as to reduce the level of leachable materials retained in the hydratable polymer after treatment. Example 8 demonstrates the efficacy of the described methods.

Example 1

A measured amount of a candidate adsorbent (0.05 g) was placed directly into a glass vial and a freshly demolded hydratable polymer in the form of a contact lens in the xerogel state, made from a copolymer of N-vinyl pyrrolidone and methyl methacrylate using allyl methacrylate as a cross-linking agent, was also placed into the vial together with 2 mL of deionized water. The vial was sealed and put through an autoclave cycle of 121° C. at 15 psi (1.0546 kg per cm$^2$) for 30 minutes. The water from the vial was then filtered through a 0.2 µm filter and analyzed for impurities by HPLC.

HPLC analysis of the filtered solution is employed because any leachable materials remaining in the filtered solution reflects the inability of the adsorbent to remove these materials from the solution. Accordingly, integration of the HPLC peaks correlates the ability of the adsorbent to adhere leachable materials thereby removing these materials from the aqueous solution and hence the hydratable polymer. Lower HPLC peak integration values correspond to better adsorbent ability.

The results of this analysis using different candidate adsorbents are set forth in Table 1 below.

TABLE 1

| ADSORBENT | HPLC ANALYSIS PEAK AREA |
|---|---|
| No Adsorbent | 4,800 |
| Activated Carbon Type RO-0.8 | 0 |
| Activated Carbon Type 12/20# | 3 |
| Activated Carbon Type 4/14# | 10 |
| Activated Carbon Type G-60100# | 0 |
| Eudragit L100-55 | 6 |
| Eudragit S100 | 4 |
| Molecular Sieves 3A | 4,900 |
| Silica Gel | 1,600 |

Activated Carbon Types RO-0.8, 12/20#, 4/14#, and G-60100# can be obtained from Aldrich Chemical Company, Milwaukee, Wisconsin. Eudragit L100-55 and S100 are acrylic polymers available from Rohm Pharma, Weiterstadt, Germany.

The above data demonstrates that activated carbon effectively removes impurities from the aqueous solution, that silica gel also removed impurities from the aqueous solution, albeit less efficiently than activated carbon, and that molecular sieves 3A do not.

In the absence of an adsorbent, the amount of impurities in the water is dictated by an equilibrium balance between the polymer and the water. In turn, adherence of the impurities to the adsorbent effectively shifts this equilibrium balance resulting in the impurities in essence being "pulled" from the polymer composition through the water onto the adsorbent. Such a process provides an efficient means to remove impurities from the polymer composition.

Example 2

This example demonstrates the correlation between integrated HPLC peak areas and the level of leachable material contamination in the hydratable polymer. Specifically, calibration curve for the HPLC analysis was developed for the N-vinyl pyrrolidone and methyl methacrylate monomers that could be present in the polymerized copolymers of N-vinyl pyrrolidone/methyl methacrylate. The relationship between HPLC peak area and quantity of monomer in water was determined by adding known amount of each of these materials to water. The correlation was determined as follows:

| HPLC Calibration | | | |
|---|---|---|---|
| N-Vinyl Pyrrolidone | | Methyl Methacrylate | |
| ppm | HPLC Peak Area* | ppm | HPLC Peak Area* |
| 0.05 | 0 | 0.05 | 9.4 |
| 0.10 | 5.4 | 0.10 | 8.3 |

-continued

HPLC Calibration

| N-Vinyl Pyrrolidone | | Methyl Methacrylate | |
| --- | --- | --- | --- |
| ppm | HPLC Peak Area* | ppm | HPLC Peak Area* |
| 0.20 | 7.8 | 0.20 | 7.8 |
| 0.40 | 24.5 | 0.40 | 10.6 |
| 0.80 | 33.6 | 0.80 | 33.7 |
| 1.60 | 54.3 | 1.60 | 26.2 |
| 3.20 | 106.0 | 3.30 | 49.7 |
| 6.40 | 218.4 | 6.60 | 87.8 |
| 12.9 | 460.2 | 13.1 | 170.0 |
| 25.8 | 964.0 | 26.3 | 345 |
| 51.6 | 2550 | 52.6 | 728 |
| 103.2 | 4096 | 105.3 | 1417 |

*Arbitrary units full scale; analysis made on a C8 column using acetonitrile/water under reverse flow conditions and detected by UV (ultraviolet) at 254 nanometers The above correlation data permits one skilled in the art to readily assess the amount of monomer (in ppm) present in the solution based on integration of the HPLC peak corresponding to these monomers. Similar correlation curves could readily be prepared for other monomers.

Example 3

The purpose of this example is to demonstrate the use of a water permeable membrane to separate the adsorbent from the hydratable polymer. The water permeable membrane is capable of retaining the adsorbent therein but permits transport of the aqueous solution there across.

Specifically, an envelope was fashioned from a 0.2 μm nylon membrane by heat sealing and a small amount of an adsorbent, 0.03 grams of activated carbon (Norit RO-0.8, available from Aldrich Chemical Company, Milwaukee, Wis., USA) was then enclosed and the envelope was heat sealed to fully contain the adsorbent. The filled envelope was then placed into a glass lens vial together with 10 freshly demolded dry lenses, made of a copolymer of N-vinyl pyrrolidone and methyl methacrylate, and a 2 mL aliquot of deionized water was added. The vial was sealed with a rubber closure and crimp seal and was then subjected to an autoclave cycle of 121° C. at 15 psi (1.0546 kg per cm$^2$) for 30 minutes. After autoclaving, the water from the vial was analyzed by HPLC and GPC for the presence of impurities and none were found.

Example 4

The purpose of this example is to evaluate the ability of an adsorbent to remove impurities from different polymer compositions. Accordingly, four different polymer compositions were treated in the manner described above for Example 1 and the recovered aqueous solution evaluated for the presence of impurities by HPLC. The results of this evaluation are set forth in Table 2 below.

TABLE 2

| LENS | HPLC PEAK AREA FOR MAIN PEAK | |
| --- | --- | --- |
| POLYMER | NO ADSORBENT | WITH ADSORBENT* |
| NVP/MMA | 5000 | 0 |
| GMA/MMA | 592 | 9 |
| HEMA | 7262 | 0 |
| DMA/MMA | 654 | 4 |

*Adsorbent in this case was activated Carbon Norit RO-0.8

The results of the above example illustrate that an adsorbent can be used to remove leachable impurities from several different polymer compositions.

Example 5

In a study using polypropylene "blister" packages, the adsorbent was retained between the lidding stock and a membrane wherein the membrane was heat sealed to the lidding stock. Such a device is illustrated in FIG. 2A and FIG. 2B. A freshly demolded lens of the type used in Example 2 above was placed into the well defined by the blister package and 2 mL of water or saline was added as shown in FIG. 2A. The blister was then sealed with the lidding stock holding the adsorbent with the adsorbent covering the well of the blister.

The blister package was then placed inverted into an autoclave and sterilized at 121° C. at 15 psi (1.0546 kg per cm$^2$) for 30 minutes as shown in FIG. 2B. Several trials with different adsorbents and lens types were analyzed in this example and the results are set forth in Table 3 below:

TABLE 3

| ADSORBENT | HPLC PEAK AREA FOR MAIN PEAKS |
| --- | --- |
| No Adsorbent | 5,600 |
| Activated Carbon Type RO-0.8 | 7 |
| Activated Carbon Type 12/20# | 370 |
| Activated Carbon Type 4/14# | 57 |
| Eudragit L100-55 | 58 |

The above example illustrates that the methods of this invention are suitable for removing leachable impurities from an ophthalmic device during storage/shipment of this device.

Example 6

A contact lens was prepared in a mold system as per U.S. Pat. No. 5,036,971 wherein the male mold half was removed after dry lens preparation, leaving the dry lens only in the female half of the mold. An aliquot of saline solution is added to the mold and the mold is then covered with a lidding stock as per Example 5 above so that the membrane containing an adsorbent covers the well of the female mold. This lens was allowed to hydrate in the packaging solution and then the packaged lens was autoclaved in the inverted portion.

The above example illustrates that the methods of this invention can be incorporated with the manufacturing process so as to simplify manufacturing of the lens, removal of contaminants and shipment for consumer use into a single overall process.

Example 7

The purpose of this example is to illustrate the advantage of heating the adsorbent/hydratable polymer/aqueous solution to enhance adsorbency of the leachable material onto the adsorbent.

In this example, an adsorbent (0.05 g) was added to individual glass vials. A contact lens made of a hydratable polymer similar to that of Example 1 above was added to each vial along with 2 mL of water. Each sample of adsorbent was conducted in duplicate so as to provide two vials containing the same adsorbent, the same type of contact lens and the same amount of water. The vials were sealed and the first vial containing the same adsorbent was maintained at room temperature for 30 minutes whereas the second vial was autoclaved at 121° C. for 30 minutes. Afterwards, the solution in each of the vials was analyzed by HPLC and the amount of leachable material remaining in the solution determined by integration of the HPLC peak area. The results of this analysis are set forth in Table 4 below:

TABLE 4

| Adsorbent | HPLC Peak Area* Room Temperature | HPLC Peak Area* 121° C. |
|---|---|---|
| Carbon 12-20 | 11 | 2.8 |
| Carbon RO 0.8 | 3 | 0 |
| Carbon 4-14 | 32 | 10 |
| Eudragit L100-55 | 559 | 23 |
| No Adsorbent | Not Done | 5003 |
| No Lens | Not Done | 0 |

*Arbitrary units full scale

The above results demonstrate that more efficient removable of leachable materials by the adsorbent is achieved at higher temperatures as evidenced by the reduction of the HPLC peak area.

Example 8

In order to demonstrate that the adsorbent removes leachable material from the aqueous solution in which the lenses have been placed and, hence, from the hydratable polymer itself, the following experiment was conducted.

Ten (10) separate lenses obtained from a hydratable polymer similar to that of Example 1 above were separately extracted in vials in the presence of activated charcoal type 12/20#, in a manner as also described in Example 1. After this extraction and hydration, each of the lenses were removed from each of the vials, rinsed quickly with deionised water and all placed into one vial. An aliquot of deionised water was then added to this vial and the vial sealed and autoclaved. The solution from the vial was then analyzed using HPLC. The quantity of extractable material measured corresponded to less than 5 ppm of material per lens. This compares to values of more than 100 ppm typically obtained for single lenses similarly extracted in the absence of an adsorbent.

The above data demonstrates that the extraction methods of this invention effectively remove leachable material from the hydratable polymers which leachable material is also removed from the aqueous solution by the adsorbent used in these methods.

What is claimed is:

1. A method for extracting unreacted monomers and partially reacted oligomers from a hydratable xerogel polymer containing said monomers and oligomers wherein said polymer after hydration is in the form of an ophthalmic device which method comprises:

(a) incorporating an adsorbent into an aqueous solution wherein said absorbent is selected from the group consisting of activated carbon, silica gel and an organic solvent forming a two-phase system with water; and (b) contacting said hydratable xerogel polymer, prior to hydration, with the solution produced in (a) above and maintaining said polymer in such contact under conditions sufficient to reduce the concentration of said monomers and oligomers in said polymer.

2. The method according to claim 1 wherein said adsorbent is separated from said hydratable polymer.

3. The method according to claim 2 wherein said separation of the adsorbent from said hydratable polymer is achieved by a water permeable membrane.

4. The method according to claim 1 wherein said aqueous solution comprises up to about 5 weight percent of a miscible organic solvent.

5. The method according to claim 1 wherein said aqueous solution is a saline solution buffered to a pH of from 6 to 8.

6. The method according to claim 1 wherein the amount of monomers and oligomers in the hydratable xerogel polymer is reduced to less than about 10 ppm.

7. A method for extracting unreacted monomers and partially reacted oligomers from a hydratable xerogel polymer containing said monomers and oligomers and hydrating said polymer wherein said polymer, and hydration, is in the form of an ophthalmic device which method comprises:

(a) incorporating an absorbent into an aqueous solution wherein said absorbent is selected from the group consisting of activated carbon, silica gel and an organic solvent forming a two-phase system with water; and (b) immersing a hydratable polymer in its xerogel form and prior to hydration thereof into the solution produced in (a) above and maintaining said polymer in said solution under conditions sufficient to reduce the concentration of said monomers and oligomers from said polymer and to hydrate said polymer.

8. The method according to claim 7 wherein said adsorbent is separated from said hydratable polymer.

9. The method according to claim 8 wherein said separation of the adsorbent from said hydratable polymer is achieved by a water permeable membrane.

10. The method according to claim 7 wherein said aqueous solution comprises up to about 5 weight percent of a miscible organic solvent.

11. The method according to claim 7 wherein said aqueous solution is a saline solution buffered to a pH of from 6 to 8.

12. The method according to claim 7 wherein the amount of said monomers and oligomers in the hydratable polymer is reduced to less than about 10 ppm.

13. A method for extracting unreacted monomers and partially reacted oligomers from a hydratable xerogel polymer containing said monomers and oligomers wherein said polymer, after hydration, is in the form of an ophthalmic device which method comprises:

(a) incorporating an adsorbent into an aqueous solution comprising water and a hydratable polymer wherein said polymer, before addition to said water, is in its non-hydrated state and further wherein said absorbent is selected from the group consisting of activated carbon, silica gel and a organic solvent forming a two-phase system with water; and (b) maintaining said polymer in said aqueous solution under conditions sufficient to reduce the concentration of said monomers and oligomers in said polymer.

14. The method according to claim 13 wherein said adsorbent is separated from said hydratable polymer.

15. The method according to claim 14 wherein said separation of the adsorbent from said hydratable polymer is achieved by a water permeable membrane.

16. The method according to claim 13 wherein said aqueous solution comprises up to about 5 weight percent of a miscible organic solvent.

17. The method according to claim 13 wherein said aqueous solution is a saline solution buffered to a pH of from 6 to 8.

18. The method according to claim 13 wherein the amount of said monomers and oligomers in the hydratable polymer is reduced to less than about 10 ppm.

19. A sealed package comprising an aqueous solution, a hydratable polymer, initially a xerogel in its non-hydrated state which after hydration is in the form of an ophthalmic device, which polymer contains unreacted monomers and partially reacted oligomer contaminants and an adsorbent wherein said package contains sufficient solution to immerse said polymer and further wherein said adsorbent has a higher affinity for said monomer and oligomers than either said polymer or the solution and still further wherein said adsorbent is selected from the group consisting of activated carbon, silica gel and an organic solvent forming a two-phase system with water.

20. The sealed package according to claim 19 wherein said adsorbent is separated from said hydratable polymer.

21. The sealed package according to claim 20 wherein said separation of the adsorbent from said hydratable polymer is achieved by a water permeable membrane.

22. The sealed package according to claim 19 wherein said aqueous solution comprises up to about 5 weight percent of a miscible organic solvent.

23. The sealed package according to claim 19 wherein said aqueous solution is a saline buffered to a pH of from 6 to 8.

* * * * *